(12) United States Patent
Michelson et al.

(10) Patent No.: US 10,043,135 B2
(45) Date of Patent: Aug. 7, 2018

(54) TEXTUAL INFORMATION EXTRACTION, PARSING, AND INFERENTIAL ANALYSIS

(71) Applicant: InferLink Corporation, El Segundo, CA (US)

(72) Inventors: Matthew Michelson, La Canada, CA (US); Steven Minton, El Segundo, CA (US)

(73) Assignee: InferLink Corporation, El Segundo, CA (US)

( * ) Notice: Subject to any disclaimer, the term of this patent is extended or adjusted under 35 U.S.C. 154(b) by 0 days.

(21) Appl. No.: 15/421,166

(22) Filed: Jan. 31, 2017

(65) Prior Publication Data

US 2017/0262430 A1 Sep. 14, 2017

Related U.S. Application Data

(60) Provisional application No. 62/305,413, filed on Mar. 8, 2016.

(51) Int. Cl.
| | |
|---|---|
| *G06F 17/27* | (2006.01) |
| *G06N 5/04* | (2006.01) |
| *G06F 19/00* | (2018.01) |
| *G16H 50/70* | (2018.01) |
| *G06F 17/30* | (2006.01) |

(52) U.S. Cl.
CPC ....... *G06N 5/048* (2013.01); *G06F 17/30719* (2013.01); *G06F 19/324* (2013.01); *G06F 19/325* (2013.01); *G06F 19/3443* (2013.01); *G16H 50/70* (2018.01)

(58) Field of Classification Search
CPC ...................................................... G06F 17/02
USPC .......................... 704/1, 9, 10, 257, 270–275
See application file for complete search history.

(56) References Cited

U.S. PATENT DOCUMENTS

| | | | | |
|---|---|---|---|---|
| 7,716,040 | B2 * | 5/2010 | Koll | G06F 17/211 704/235 |
| 2003/0105638 | A1 * | 6/2003 | Taira | G06F 17/2881 704/275 |
| 2008/0071746 | A1 | 3/2008 | Concordia et al. | |
| 2009/0319515 | A1 | 12/2009 | Minton et al. | |
| 2010/0114789 | A1 | 5/2010 | Dane | |
| 2010/0313258 | A1 * | 12/2010 | Chaudhuri | G06F 17/278 726/9 |

(Continued)

OTHER PUBLICATIONS

Hahn et al. "MEDSYNDIKATE—a natural language system for the extraction of medical information from findings reports". International Journal of Medical Informatics 67, 2002, pp. 63-74.*

(Continued)

*Primary Examiner* — Jesse Pullias
(74) *Attorney, Agent, or Firm* — Carr & Ferrell LLP (57) ABSTRACT

Textual information extraction, parsing, and inferential analysis systems and methods are provided herein. An example method includes extracting content for each of a plurality of types from a corpus of textual information, the plurality of types corresponding to segments of an inference scheme, the inference scheme including a dependency that orders the segments together so as to create a summation of the corpus of textual information when the extracted content is assembled, and assembling one or more inferred statements using the inference scheme and the extracted content.

17 Claims, 9 Drawing Sheets

(56) References Cited

U.S. PATENT DOCUMENTS

2015/0127565 A1    5/2015  Chevalier et al.

OTHER PUBLICATIONS

Cuesters W. "Medical natural language understanding as a supporting technology for data mining in healthcare". In: KJ Cios (ed.) Medical Data Mining an Knowledge Discovery, Physica-verlag Heidelberg, New York, 2001;:41-67.*

* cited by examiner

| Ratio Result | "11 of 34 patients"; "7/23" |
| --- | --- |
| Percent Result | "87%"; "23 pct. of patients" |
| Population: Direct | "118 patients given IFX"; "Infliximab (n=27)" |
| Population: "Each" | "88 patients in each treatment group" |
| Population: Randomized | "150 patients were randomly assigned to IFX or placebo" |
| Disease Extractor | "123 patients with Crohn's Disease" |
| Intervention Extractor | "given budesonide" "received placebo" |
| Named Group Extractor | "Patients in Group A (infliximab)" |
| Outcome Extractor | "in remission," "exhibited adverse events" |

FIG. 4B

Enter text and hit enter:

Budesonide (BUD) is a potent steroid that undergoes extensive first-pass metabolism. The aim of this study was to compare the efficiency and safety of BUD and prednisone (PRED) in the treatment of active Crohn's disease involving the terminal ileum and/or the colon. One hundred patients received BUD, and 110 patients received PRED. By intention-to-treat analysis, treatment efficacy defined as Crohn's Disease Activity Index of <150 was 48% and 50% for the BUD and PRED groups, respectively.

Ratio Results:

| 48 | 100 | budesonide | efficacy | crohn disease | |
| 55 | 110 | prednisone | efficacy | crohn disease | |

TEXTUAL INFORMATION EXTRACTION, PARSING, AND INFERENTIAL ANALYSIS

CROSS REFERENCE TO RELATED APPLICATIONS

This application claims the benefit and priority of U.S. Provisional Application Ser. No. 62/305,413, filed on Mar. 8, 2016, which is hereby incorporated by reference in its entirety, including all references and appendices cited therein. This application is related to U.S. Provisional Application Ser. No. 62/415,681, filed on Nov. 1, 2016, which is hereby incorporated by reference herein in its entirety, including all references and appendices cited therein.

STATEMENT REGARDING FEDERALLY SPONSORED RESEARCH OR DEVELOPMENT

This invention was made with government support under Grant No. 1R43LM012210-01 REVISED (Federal Award Identification No. R43LM012210) awarded by the National Institutes of Health. Accordingly, the United States government has certain rights in this invention.

FIELD OF INVENTION

The present technology relates generally to computer software, and, more particularly, to systems and methods for computationally harvesting medical evidence about treatments and protocols from medical literature, including, but not limited to, the population sizes for different treatment groups, the effectiveness of the therapies, the disease(s) or issue(s) treated, and the interventions applied in the studies.

SUMMARY

According to some embodiments, the present disclosure is directed to a method, comprising: (a) extracting content for each of a plurality of types from a corpus of textual information, the plurality of types corresponding to segments of an inference scheme, the inference scheme comprising a dependency that orders the segments together so as to create a summation of the corpus of textual information when the extracted content is assembled; and (b) assembling one or more inferred statements using the inference scheme and the extracted content.

According to some embodiments, the present disclosure is directed to a method, comprising: (a) a processor; and (b) a memory for storing executable instructions, the processor executing the instructions to: (i) execute a plurality of extractor modules to extract evidence from each of a plurality of types from a medical study, the plurality of types corresponding to segments of an inference scheme, the inference scheme comprising a dependency that orders the segments together so as to create a summation of the medical study when the extracted evidence is assembled; and (ii) execute an assembly module that assembles one or more inferred statements about the medical study using the inference scheme and the extracted evidence.

According to some embodiments, the present disclosure is directed to a method, comprising: (a) processing input text from medical papers or medical abstracts to extract pieces of evidence, including treatment results, population details, interventions used, outcomes studied, and diseases targeted; (b) associating the extracted pieces of evidence within individual medical papers or medical abstracts to produce a structured representation of a study's results; and (c) combining results from more than one separate medical paper or separate medical abstract to produce an aggregate summary of the evidence.

According to some embodiments, the present disclosure is directed to non-transitory computer-readable medium comprising computer readable code, which when executed by one or more processors, implements a method for automatically extracting medical evidence from medical papers and medical abstracts, the method comprising: (a) processing input text from medical papers or medical abstracts to extract pieces of evidence, including treatment results, population details, interventions used, outcomes studied and diseases targeted; (b) associating the extracted pieces of evidence within individual medical papers or medical abstracts to produce a structured representation of a study's results; (c) combining results from more than one separate medical paper or separate medical abstract to produce an aggregate summary of the evidence.

BRIEF DESCRIPTION OF THE DRAWINGS

The accompanying drawings, where like reference numerals refer to identical or functionally similar elements throughout the separate views, together with the detailed description below, are incorporated in and form part of the specification, and serve to further illustrate embodiments of concepts that include the claimed disclosure, and explain various principles and advantages of those embodiments.

The methods and systems disclosed herein have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

DETAILED DESCRIPTION

The present disclosure relates to a technological improvement in content extraction and inference-based creation of content summaries from literature such as medical studies.

The following paragraphs provide context and example use cases for the systems and methods of the present disclosure. These descriptions are intended to be non-limiting and are provided for example and context.

In order for doctors to stay updated on the latest, effective therapies, and in order to build updated guidelines and protocols via systematic review or meta-analysis, there needs to be a repository of medical evidence, refreshed as new literature is published, and in which the details from medical studies are extracted from the literature and represented in a structured form that is easy for both machines and people to analyze. By automatically extracting treatment data from the medical literature, such a structured data set of evidence can be created at a scale covering all of the published literature. The structured data set of evidence can be refreshed and updated as new medical information is published.

The systems and methods of the present disclosure increase the availability and dissemination of evidence from published literature of randomized controlled trials (RCTs). By automatically combining the evidence from trials via meta-analysis (sometimes also called meta-study), an overall effect can be determined, which in turn, can yield new or updated treatment guidelines or new research directions. As such, meta-analysis is fundamental to aggregating evidence in evidence-based medicine.

The present disclosure describes systems and methods that implement information extraction algorithms that are capable of extracting components of medical publications from within papers at scale, including interventions used and their efficacy, population information, and the outcomes targeted, as well as other similar evidence types.

The ability of the systems and methods disclosed herein to extract information from medical literature for meta-analysis in the present disclosure involves natural language processing (in particular, an ability to both accurately extract for the processing of many millions of documents in parallel).

The systems and methods herein continually locate medical literature from various known repositories, extract the results from new papers, and update a database of evidence. Medical researchers can leverage the database of evidence to rapidly create meta-studies across a large number of diseases, interventions, and outcomes. The systems and methods herein provide a web-based user interface that can be used to refine or update extracted evidence/content, add user-defined evidence, and automatically perform statistical analyses to generate a meta-study result. Further, as new evidence related to a previous study is encountered, the systems can alert the researcher and a corresponding meta-study can be updated accordingly.

In some embodiments, a meta-analysis combines results from multiple studies on the same (or similar) diseases, interventions and outcomes, and analyzes the aggregated results using statistical techniques. These parameters are referred to herein as types. Thus, there is a disease type, an intervention type, an outcome type, and so forth. Each medical document will include these types. For example, a medical study that involves the testing of a new drug for reducing neuropathy from diabetes may include a disease type of diabetes, an intervention of a drug name, and an outcome type of percentage of reduction in neuropathy symptoms.

The systems and methods of the present disclosure can advantageously improve dissemination of research results via meta-studies that will support advancement of evidence-based medicine, leading to updates in clinical guidelines. This is especially valuable in the case of quickly changing evidence, where more rapidly updated meta-studies can be reflected in clinical care sooner. Second, broader coverage of medicine should enable new research paths and directions. Creating meta-studies for uncommon diseases using the systems and methods disclosed herein will help researchers who would otherwise miss individual results buried in the literature. Even popular disease areas can benefit, as the myriad of papers published on popular topics can quickly overwhelm researchers, while meta-studies can help synthesize the information and suggest new routes of research.

The present disclosure provides systems and methods that leverage artificial intelligence and medical expertise in meta-analysis. These systems and methods also allow for meta-study creation that is scalable and more transparent. By automating the meta-study process, this allows for potential coverage of the full set of topics within the medical literature. Further, as new results are published, they can immediately become incorporated into the appropriate meta-studies. This will dramatically lower the cost and increase the speed and coverage of meta-analyses, resulting in a greater dissemination of research results, with updates in a timely manner.

While there are efforts to standardize trial data, for instance, via ClinicalTrials.gov, adherence to such standards is lacking. For example, only 9% (164/1835) of the records under the Inflammatory Bowel Disease section of ClinicalTrials.gov provide actual, numeric results. Information extraction technology can be leveraged to perform this task.

The systems and methods disclosed herein utilize algorithms that logically associate components of a result with one another. For instance, one sentence might provide, "12 of 14 patients in Group A were in remission," while another sentence states, "Patients in Group A were given budesonide." In this case, the systems and methods associate an efficacy ratio 12/14 (one type of extracted information) with an intervention "budesonide" (a second type of extracted information) and the outcome "remission" (a third type of extracted information) although those were cross-sentential mentions (e.g., included in separate sentences but within the same document).

The systems of the present disclosure comprise an ensemble of machine learning modules, each specializing in different linguistic analysis. For instance, one module can parse sentences related to how patients are randomly assigned into groups, while another parses the outcomes of studies. Their results are then linked logically, to create a structured representation of the results of the studies. In some embodiments the logical linking can be defined by an inference schema that includes a plurality of segments that are linked together based on dependencies.

The systems of the present disclosure also utilize a suite of statistical measures used in meta-analysis, written in Scala, a modern programming language. Machine learning methods such as pattern relaxation, ensemble learning and eventually, deep learning are utilized, and modern data processing pipelines are implemented to create a novel framework for turning medical text into structured results, which can be combined for meta-analysis.

The systems and methods of the present disclosure can also account for extraction failures that are due to a lack of pattern coverage. For instance, the system can detect differences between the phrases "patients undergoing hematopoietic stem cell transplantation" and "hematopoietic stem cell transplantation," but determine that both phrases represent an intervention.

In some embodiments, the systems and methods can group together studies by intervention and outcome. In order to facilitate meta-studies, these systems and methods harvest the results from the text. These results are grouped results across different studies. For instance, a meta-study focusing on remission in Crohn's disease should group together studies that focus on that outcome (remission) for that disease (Crohn's). This grouping allows the systems to collect extracted results on the same topic from multiple papers, as input to the meta-analysis calculations.

In some embodiments, the systems and methods herein employ various techniques for meta-analysis, which include statistical algorithms for random effects models (including Q-Statistics, the Paule-Mandel model, and the DerSimonian and Laird model) and also other common reporting metrics such as relative risk and its confidence interval.

In some embodiments, the systems and methods of the present disclosure can create, in a semi-automatic way, meta-studies. Once papers have been processed, such that all of the results have been extracted, a user can query the system by any combination of disease, outcome, intervention(s) and the system will automatically group together all of the studies that match the user query. The system will then employ the meta-analysis techniques, including random effects models and other common reporting metrics, providing the user with an automatically generated meta-study, on-the-fly, complete with all citations of the underlying results.

In some embodiments the systems and methods herein employ algorithms process data within a Hadoop file system, which stores input data (such as medical abstracts) in a huge, parallel, highly accessible manner. This comprises a data layer of the systems. The system can also utilize parallel processing architectures that run on a distributed cluster of computers, resulting in a highly scalable technical infrastructure.

In some embodiments, the systems herein are tuned through algorithms currently capable of processing 1,000,000 medical texts per day. Algorithms generalize to different diseases with comparable performance, without requiring any re-configuration.

Embodiments of the present disclosure are directed to systems and methods for computationally extracting medical evidence in the form of study details, including but not limited to, the effectiveness of treatment, the treatment group details, and the level of evidence, directly from the medical literature.

In some embodiments, extraction algorithms can pull specific medical evidence from the written medical literature, turning the language into structured data, using statistical inference. Extraction algorithms may be techniques for automatically pulling out words, phrases or numbers that represent a specific data point of interest (e.g., a type).

Structured data may be data that is put into a particular, well-defined format, such as a database. Medical evidence may be information about studies published in the literature, including information such as what treatments were used, what treatments were compared, details about the study populations, treatment effectiveness, treatment outcomes, and diseases targeted. In some embodiments, evidence for similar diseases and interventions can be grouped together for analysis.

Figure 1:
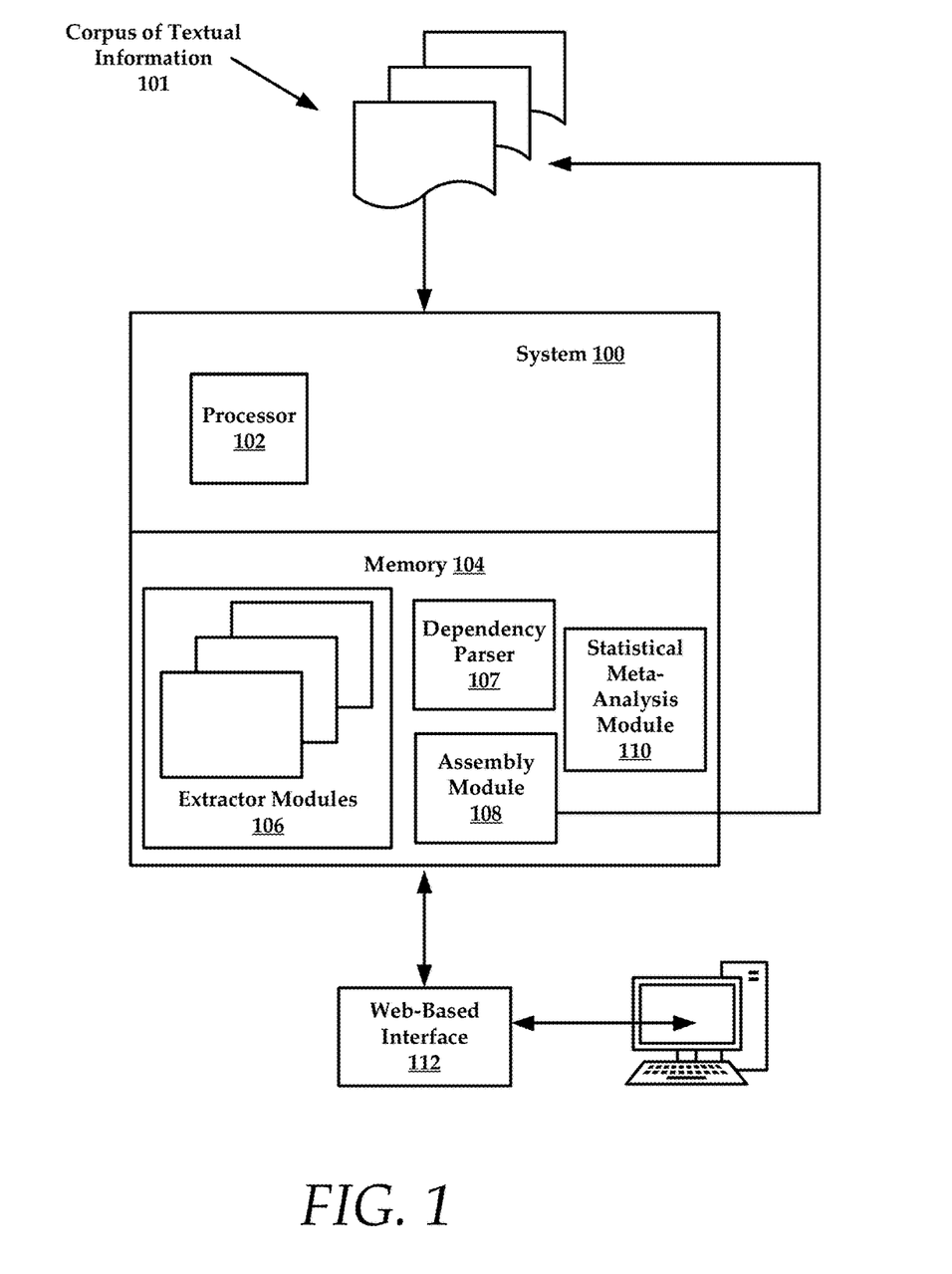
FIG. 1 illustrates an exemplary system used to practice aspects of the present disclosure and that is constructed in accordance with embodiments disclosed herein.

The foregoing paragraphs provide context and example use cases. The following paragraphs provide details regarding various technical implementations that are used to practice aspects of the present disclosure. FIG. 1 is a schematic diagram of an example system 100. The system 100 generally comprises a processor 102 and memory 104 that stores instructions. In some embodiments, the memory 104 stores various modules such as a plurality of extractor modules 106, a dependency parser 107, an assembly module 108, and a statistical meta-analysis module 110. In some embodiments, the system 100 provides a web-based user interface 112 that allows users to interact with the system 100. The system 100 receives textual content such as medical literature from a corpus of textual information 101.

Figure 2:
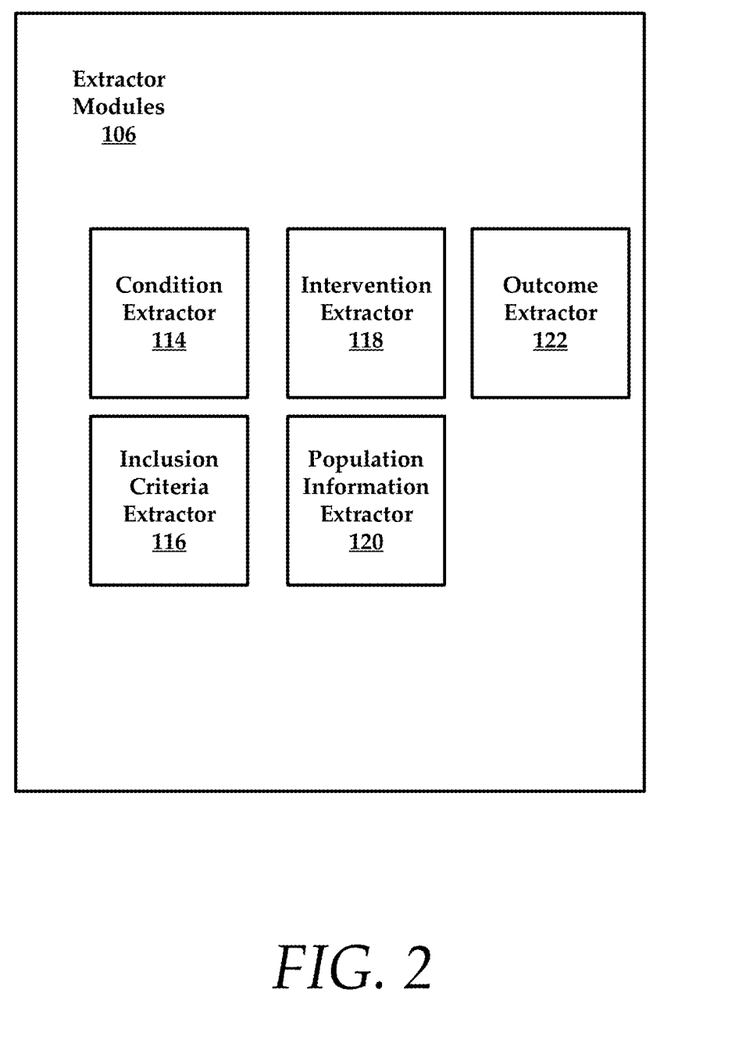
FIG. 2 is a schematic block diagram of an example set of extractor modules for use in a system of the present disclosure.

FIG. 2 illustrates a detailed schematic view of an example plurality of extractor modules 106. The plurality of extractor modules 106 comprises, in various embodiments, a condition extractor 114, an inclusion criteria extractor 116, an intervention extractor 118, a population information extractor 120, an outcome extractor 122. These are merely examples of extractors and the number and type of extractors can vary according to the types of information/content/evidence that a user desires to extract from digital content such as medical studies.

According to some embodiments, each extractor is associated with a unique type. For example, the types would comprise a condition, an inclusion criterion, an intervention, a population size, and an outcome. By way of example, these types are common types of information or evidence that can be extracted from a medical study and then combined together through the use of an inference schema (e.g., dependency algorithm(s)) to create an accurate and concise evidence summary of the medical study. Advantageously, this process can be used across numerous studies and a singular, concise evidence summary can be created that is reflective of the evidence included in these numerous studies.

In some embodiments, the plurality of extractor modules 106 will receive one or more digital documents from the corpus of textual information 101. The documents processed by the plurality of extractor modules 106 can also be referred to as a corpus of informational content. Again, this corpus of informational content could include various medical studies for which a summary of evidence is desired. After the one or more digital documents are received, the plurality of extractor modules 106 are executed to extract content/evidence for each of a plurality of types from a corpus of textual information (e.g., medical documents). For example, the one or more digital documents could comprise a study describing the efficacy of a diabetes drug on treating blood sugar in a group of patients.

In one embodiment, the plurality of types correspond to segments of an inference scheme. The inference scheme comprises a plurality of segments such as intervention, condition, outcome, and inclusion. A logical dependency is created between these segments. For example, to create a concise and readable summary of evidence, the segments are ordered. By way of example, the aforementioned segments can be arranged as follows: condition, inclusion, intervention, and outcome.

A dependency algorithm orders segments together so as to create a summation of the corpus of textual information when the extracted content is assembled, as determined by the arrangement above. In some embodiments, the dependency algorithm is specified by the end user. Thus, the end user can select which segments (which directly correspond to types extracted from the medical study/studies) are extracted from the informational content. For example, a plurality of segments that correspond to types are provided in an example ordering: (condition; inclusion criterion; intervention; population size; outcome). A user may not be interested in locating all of these segments. Thus, the user can change the inferential schema and its segments to include a different ordering: (condition; intervention; outcome).

Thus, using the inference scheme, the plurality of extractor modules 106 is defined. In some embodiments, the plurality of extractor modules 106 can implement various parsing algorithms and deep learning to find words and phrases in the informational content that can be assembled into an inferential summary of content/evidence.

In one embodiment, the plurality of extractor modules 106 are configured to tag parts of speech for words within the corpus of textual information that correspond to one or more of the plurality of types. This algorithm allows the plurality of extractor modules 106 to identify words that are likely to be a type/segment in the inference scheme and ignore words that are likely not to be a type. For example, indefinite articles and other similar words can be identified and excluded. In some embodiments, the plurality of extractor modules 106 assigns each word a part-of-speech tag. The plurality of extractor modules 106 can also combine certain, multiple parts-of-speech into "chunks" which are noun phrases or verb phrases, for example. This allows the plurality of extractor modules 106 to extract textual content such as "NP patients," which means that any noun-phrase followed by the word "patients" might represent some inclusion-information for the population (e.g., an example type).

In one embodiment, the plurality of extractor modules 106 are configured to locate phrase chunks within the corpus of textual information that correspond to one or more of the plurality of types. For example, the plurality of extractor modules 106 are configured to extract words corresponding to one or more types using a command such as "*infection" which captures, for example, "cranial infection," "bacterial infection," and "blood infection" for an outcome type.

In some embodiments, the plurality of extractor modules 106 are configured to determine synonyms for at least a portion of the words. This process can leverage the statistical meta-analysis module 110 and a statistical process to find words with similar meaning by pre-processing (analyzing) a corpus of documents. The system 100 is thus trained to recognize that "infection" has a similar word meaning to "bedsores" or "bleeding," based on the fact that these words all occur with other similar words such as "patients developed X". The word-embeddings are leveraged to extract types like the outcome type by requesting "all words like infection" as a query or input to the plurality of extractor modules 106.

In one non-limiting example, the plurality of extractor modules 106 process different types where a type might be a numeric result (e.g., 11/24, 45%), population information (e.g., size of group, inclusion criteria (e.g., "diabetic patients"), exclusion criteria, etc.), outcomes (e.g., infection, remission, etc.) and diseases—just to name a few. Thus, the plurality of extractor modules 106 can extract various types of information such as numerical, textual, and so forth.

The aforementioned processes describe example extraction algorithms that are used to extract various words and phrases that are indicative of types that will, in turn, correspond to the inference schema selected. After content has been extracted from the textual informational content, the system 100 can utilize the dependency parser 107 to perform an inferential analysis.

In some embodiments, the dependency parser 107 provides customized dependency parsing. For example, the dependency parser 107 is configured to recognize the parsed segments/types and create inferential summaries of the same. For example, the dependency parser 107 can recognize a type of parse (e.g., the sentence "Drug Z, Drug W, Drug Y achieved remission 12%, 15%, and 18%, respectively" as the parse "intervention, intervention, intervention, result, result, result) and based on the recognition, assigns dependencies (Drug Z gets 12%, Drug W gets 15%, Drug Y gets 18%).

The dependency parser 107 cooperates with the assembly module 108 to create the summary of evidence. In some embodiments, this cooperative process comprises identifying all of the parsed words and phrases and then conducting logical inferences based on the parsing. In some embodiments, the dependency parser 107 can work cross-sententially (across sentences) because it processes based on extractions from the extraction process, not just the sentences as a whole. Thus, as types are extracted, these extractions are used to inform additional processing of the sentences. By way of example, if the phrase "102 patients given budesonide" is extracted, and later, "Budesonide patients had adverse events 10% of the time" is extracted, the system knows that ten patients had adverse events because of the cross-sentential logic.

Thus, in some embodiments, the assembly module 108 is configured to assemble one or more inferred statements using the inference scheme and the extracted content.

In one or more embodiments, the system 100 can utilize combined extractors, based on pattern relaxation techniques (Hearst 1992) with a logical framework for linking component results (which we refer to as the "Linker"). One novel aspect includes the assembly module 108 that employs ensemble learning to combine extractions from multiple Hearst-pattern learners using logical constraints. In some embodiments, the assembly module 108 is flexible so that it can combine extractions from arbitrary algorithms, including deep learning methods, in addition to Hearst-patterns.

The assembly module 108 can also generate meta-studies that include the assembled inferential summaries and provide the same for consumption and inclusion into the corpus of textual information 101, which can include medical literature and studies.

In sum, the system 100 is specifically configured to utilize the extracted types and logical dependencies of the inference scheme that is selected, to create a summation of the medical study (or other textual content) when the extracted evidence is assembled according to the dependencies in the inference scheme. Again, while this methodology has been described relative to use in extracting and evaluating medical studies, the present disclosure is not so limited. That is, the textual information processing described herein provides specific technical improvements in the areas of digital document processing, parsing, extraction, and similar technical fields.

The system 100 can not only process individual studies and combinations of studies, the system 100 can continually refine summaries created from these studies when other studies having similar content are received and processed by the system 100. In this way the system 100 provides dynamically evolving summaries that are up-to-date and highly relevant. In sum, the system 100 can not only create a study based on a user's query/request, but can also continuously combine results of relevant studies, automatically, to create new results (such as where the system 100 examines all combinations of studies for a disease to identify new interventions and outcomes combinations that are valid). Thus, the system 100 continuously combines studies to generate new summaries of evidence.

In some embodiments, the system 100 provides summaries that include information that is either incorrect or is not arranged into a summary that is logical and concise. For example, the system 100 may incorrectly assemble types into a summary such as transposing types. By way of example, instead of producing a correct summary of "Drug Z gets 12%, Drug W gets 15%, Drug Y gets 18%" the system 100 creates a summary of "Drug Z gets 15%, Drug W gets 12%, Drug Y gets 18%." The user can identify this error and update the types of the inferential summary.

When an error correction is received, the system 100 can use this correction to update the algorithms used by the plurality of extractor modules 106 and dependency parser 107 so that similar errors are not repeated in subsequent analyses.

In some embodiments, the system 100 allows users to use the web-based user interface 112 for interacting with results (e.g., inferential summaries) extracted from one or more studies that enable users to correct results, augment the results, or assess overall treatment effectiveness.

In various embodiments, in which the user highlights and/or presents new results in an inferential summary that the system 100 missed (either in extraction or during dependency parsing), the system 100 modifies parsing and dependency patterns used (for extraction) or the logical assignment (for dependency parser) to correct similar mistakes in subsequent analyses.

In another user feedback scenario, if the system 100 is unable to extract a suitable word or phrase from a document (s) that corresponds to a type required in an inferential scheme, a user can provide feedback to assist the system 100. In one embodiment, the feedback comprises an identification of a keyword within the corpus of textual information that is identified as being a word that belongs to the at least one of the plurality of types. The system 100 can incorporate this feedback in order to update its extraction and dependency algorithms.

The following paragraphs describe example methodologies and flowcharts that can be implemented in order to provide the extract, dependency, and summary assembly features described in additional detail herein.

Figure 3:
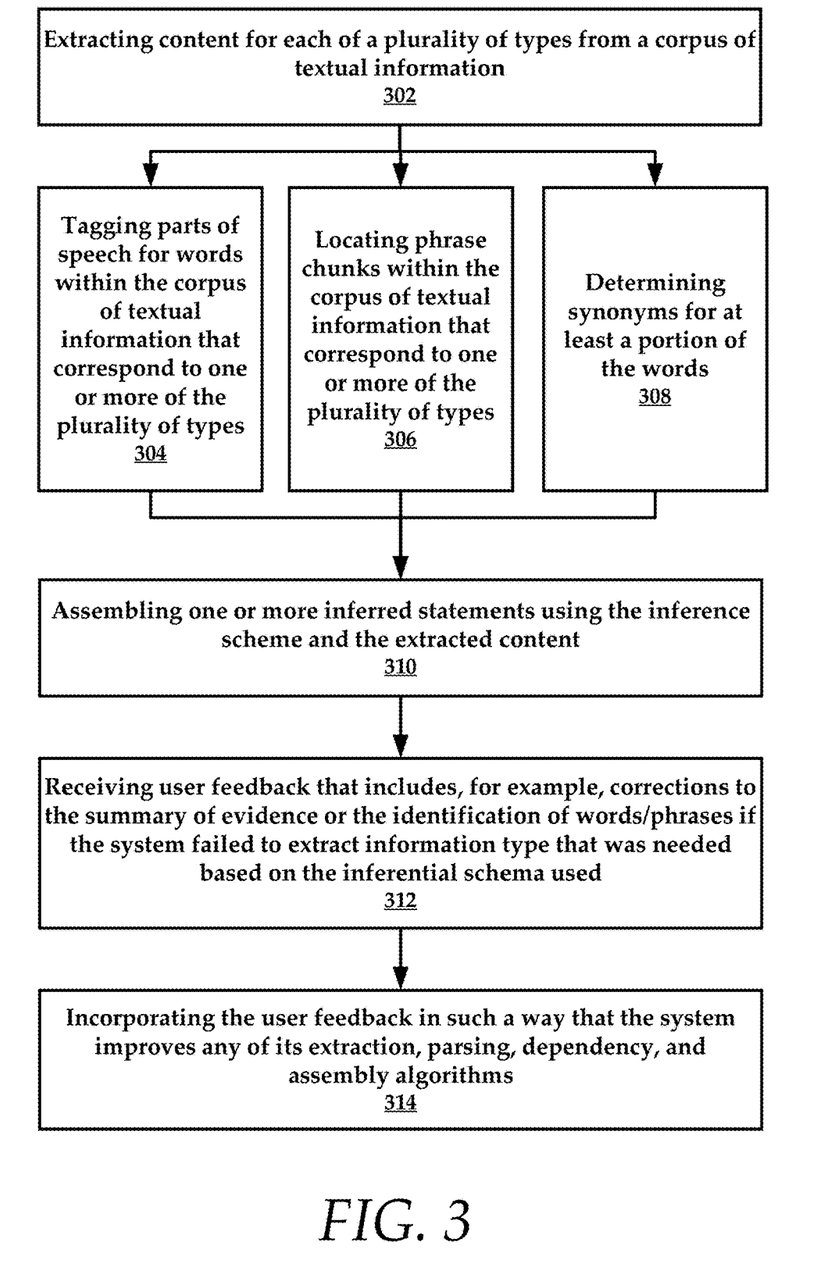
FIG. 3 illustrates an exemplary method for extracting, parsing, and assembling inferential statements in accordance with the present disclosure.

Referring now to FIG. 3, a method of the present disclosure includes a step 302 of extracting content for each of a plurality of types from a corpus of textual information. Examples of types comprise, for examples, any of a condition, an inclusion criterion, an intervention, a population size, and an outcome. The corpus of textual information can include any digital medical literature, for example.

In some embodiments, the plurality of types correspond to segments or parts of an inference scheme. The inference scheme comprises dependencies that describe an ordering of the segments together. The extracted content can be assembled using the inference scheme so as to create a summation of the corpus of textual information.

In accordance with the present disclosure, the step 302 of extracting can include the sub-steps 304-308 of tagging parts of speech for words within the corpus of textual information that correspond to one or more of the plurality of types, as well as locating phrase chunks within the corpus of textual information that correspond to one or more of the plurality of types, and determining synonyms for at least a portion of the words (also referred to as word-embedding analysis).

When the desired content has been extracted, the method includes a step 310 of assembling one or more inferred statements using the inference scheme and the extracted content. This includes creating a summary of evidence from one or more medical studies.

In some instances, the summary of evidence or summaries created may require modification by an end user. In these embodiments, the method can include a step 312 of receiving user feedback that includes, for example, corrections to the summary of evidence or the identification of words/phrases if the system failed to extract information type that was needed based on the inferential schema used. For example, the system may not locate a population type within the document but the user may be able to locate the population type. This could be due to any number of factors such as poor document quality, grammatical errors, language translation issues, and so forth. The method then includes a step 314 of incorporating the user feedback in such a way that the system improves any of its extraction, parsing, dependency, and assembly algorithms.

Again, while these methods described above have been disclosed as being applicable to analyzing medical documents, the applicability of this disclosure is not so limiting. Additional examples of medical document processing are illustrated and described below.

Figure 4A:
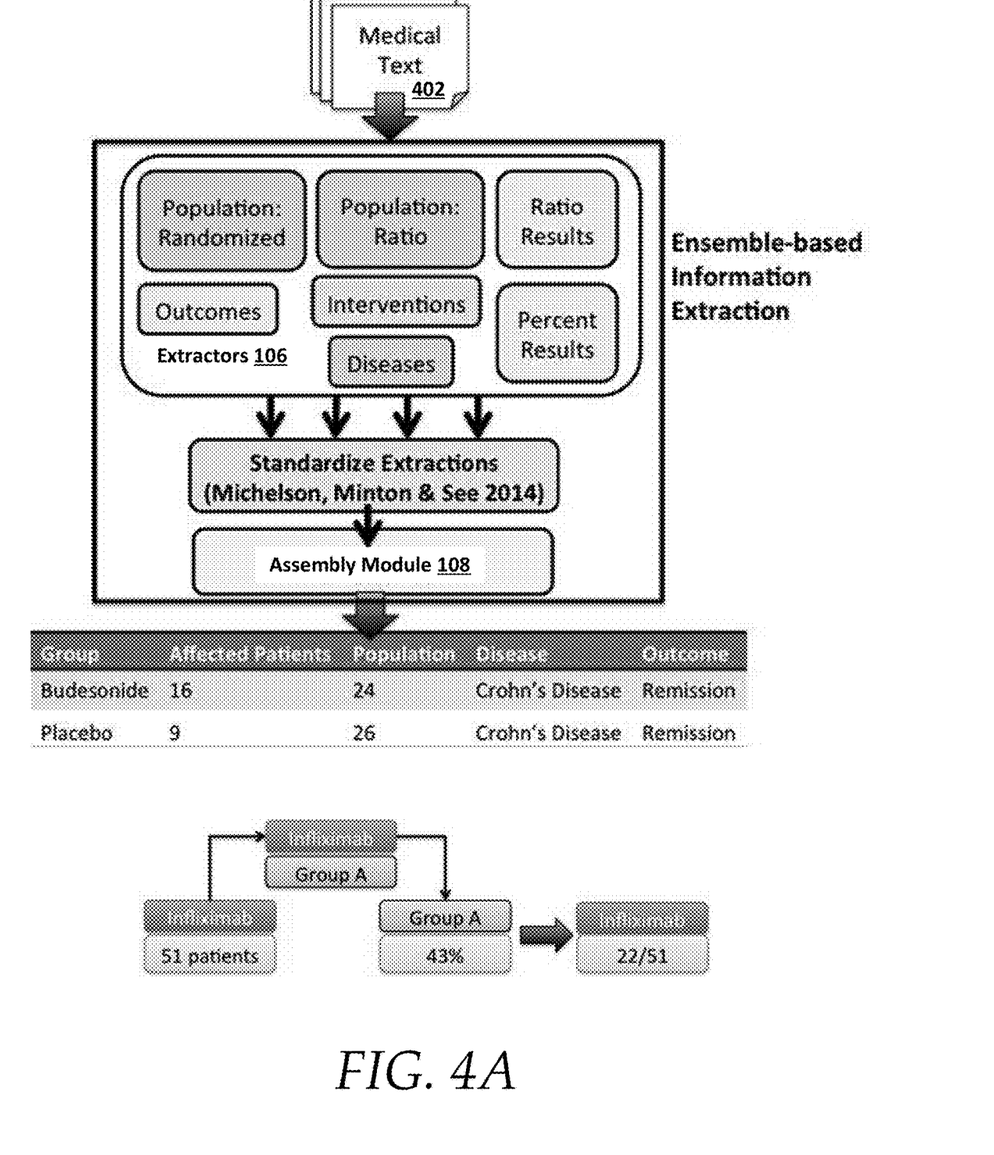
FIG. 4A illustrates another example method for extracting, parsing, and assembling content from textual content.

FIG. 4A illustrates an example extraction method. In some embodiments, the system 100 processes input text 402 (e.g., a medical text) by first applying multiple independent extractors. Each of these extractors targets a component of the result, such as extracting ratios or population information. These extracted components are then passed to the assembly module, which ties them together, using logical dependencies as defined in the inferential schema, into a whole result referred to as an inferential summary. As an example, consider the sentences (which the system correctly parses): One hundred and two patients were randomly assigned to either Group A (given Infliximab) or Group B (given placebo). 43% of Group A patients and 9% of Group B patients attained remission.

An extractor extracts out 43% efficacy for Group A and 51 as the population size for Infliximab (it interprets "random assignment" correctly), and the assembly module associates Group A and Infliximab together, outputting a correct ratio of 22/51.

Computing this ratio result requires the claimed invention's approach to interpret random group assignment, link groups to interventions, and interpret the percentage as a ratio, all of which the system 100 performs correctly.

Structuring of the result is important because random effects models, used for meta-analysis, rely on odds ratios. The system 100 can normalize extracted results to that form, and therefore the assembly module must be able to make these associations.

Figure 4B:
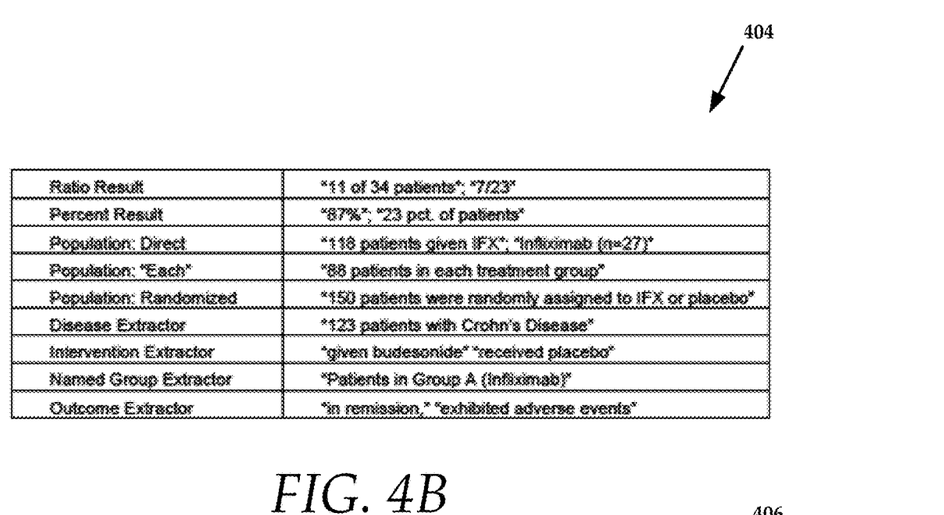
FIG. 4B is a table of information extracted from medical literature using the systems and methods disclosed herein.

In one embodiment, ten extraction modules (with roughly five patterns each) are utilized, and their outputs are enumerated in Table 404 illustrated in FIG. 4B.

Figure 4C:
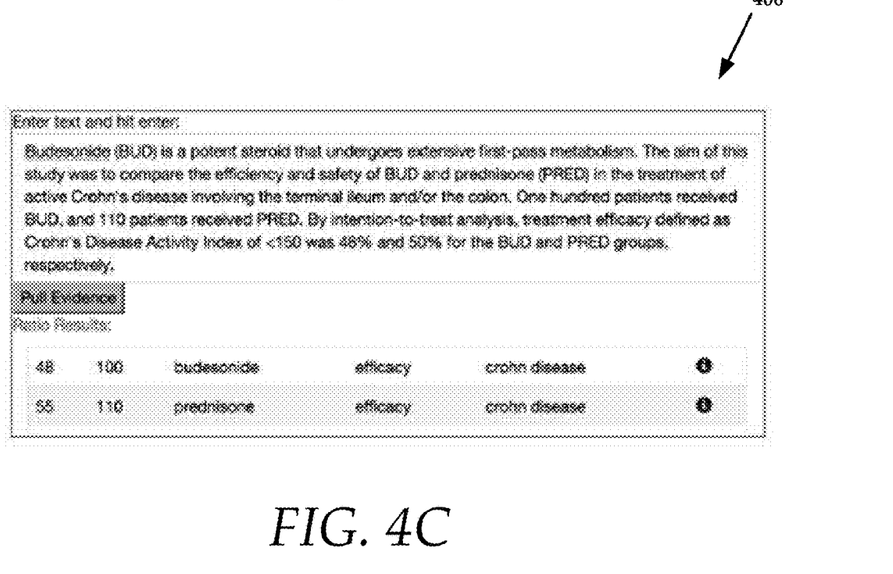
FIG. 4C illustrates an application of the methods of the present disclosure for processing cross-sentential information.

In FIG. 4C, an example of cross-sentential analysis is illustrated. The system 100 can process extremely complicated sentences where unconstrained language analysis techniques might fail. FIG. 4C illustrates in screenshot 406, correct, final ratio results that required combining cross-sentential information about interventions (including their acronyms), populations, and numeric results to compute the ratios.

Figure 5:
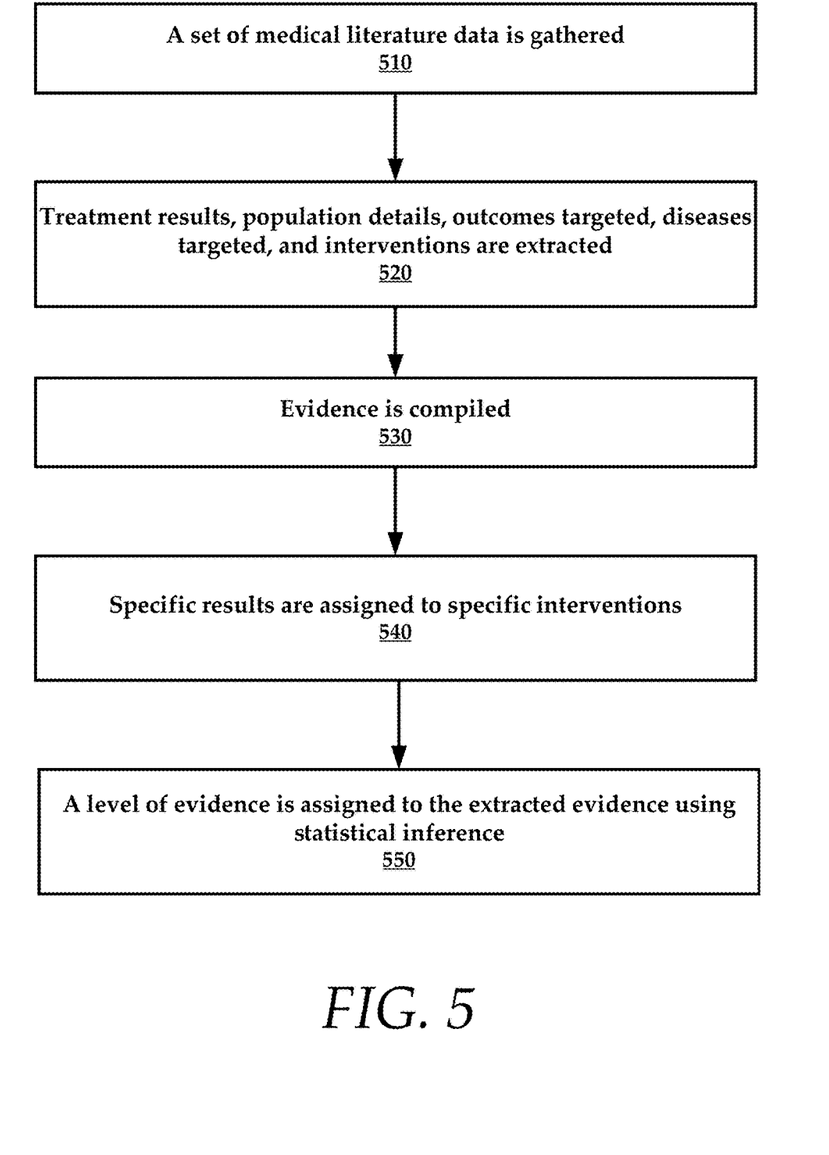
FIG. 5 is a flowchart of an example method of the present disclosure.

FIG. 5 illustrates an exemplary method to extract medical evidence from medical literature. In step 510, a set of medical literature data is gathered. Medical literature may be medical papers or medical abstracts. By processing a large number of publicly and/or privately available papers, a large set of medical evidence can be gathered. Medical evidence may be the combination of treatments tested (including placebo), the treatment effectiveness, the outcome, and the target disease. Each paper or abstract is processed separately so that each piece of evidence from each paper or abstract represents evidence from only that paper or abstract and is stored as a single unit separate from other pieces of evidence.

Information that constitutes evidence is then extracted in step 520, the information including treatment results, population details, outcomes targeted, diseases targeted, and interventions used. Treatment results may be a numeric representation of the effect of each treatment, for example, "3 out of 10." Population details may be information about the different populations in the study, for example, the size and composition details of each population. Outcomes targeted may be the end point studied in each paper, for example, the induction of disease remission. Diseases targeted may be specific or general names for a type of disease, for example, Crohn's disease. Interventions may be the therapies or other methods studied, for example, the names of a medication, a "placebo," a protocol followed, or a surgical type. Each of these types of information is extracted using an extraction algorithm trained for that type of data. For example, a result extraction algorithm can extract results in various forms, for example, those presented as ratios, percentages or values compared using a phrase such as "versus." Using a combination of statistical inference and pattern matching, each extraction algorithm can associate words in the paper or abstract with the extraction type and the extraction value. For example, if the algorithm sees the phrase "treatment A resulted in remission for 3 of 10 patients," the algorithm will associate the ratio 3/10 with a result type of extraction.

Given all of the data extracted from the text, for example, the results, the outcomes, and the interventions, the evidence is compiled together in step 530. Using statistical inference, each extracted result is assigned to the appropriate intervention and outcome. For example, in the phrase "treatment A resulted in remission for 3 of 10 patients," the result 3/10 will be assigned to the outcome "remission" and the intervention "A." Additionally, some results may need to be transformed, for example, turning a percent result into a ratio by assigning the information about the overall size of the population, and then multiplying the percent result by the total population size, to create a ratio result. Also, some information is found in multiple sentences, and the data needs to be associated across the sentences. For instance, the interventions may be described in one sentence, and the results described in another sentence, and the statistical inference can assign each result to the correct intervention.

Given the assigned results, outcomes, and interventions, the diseases targeted are extracted and assigned using statistical inference and a database of known diseases, in step 540. Unlike step 530, where specific results are assigned to specific interventions, the diseases in step 540 are assigned to all extractions from step 530.

In step 550, a level of evidence is assigned to the extracted evidence using statistical inference. For example, a paper or abstract that is a "multi-center" and "randomized" and "controlled" trial will have a higher level of evidence than one that is "single center" and, which in turn, has higher evidence than an "observational study." There may be four levels of evidence, where level 1 would be the best, most conclusive evidence, and level 4 would be the least conclusive evidence.

Figure 6:
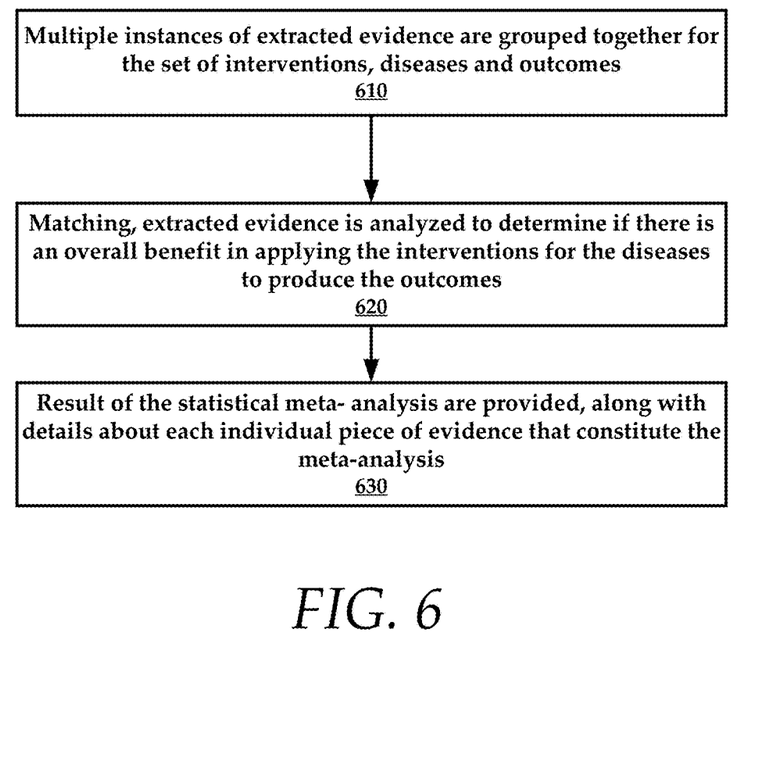
FIG. 6 is a flowchart of another example method of the present disclosure.

FIG. 6 illustrates an exemplary method to construct and compare evidence about the overall benefit, or lack thereof, for particular interventions targeting certain diseases and outcomes, based upon multiple instances of extracted evidence.

In step 610, multiple instances of extracted evidence are grouped together for the set of interventions, diseases and outcomes to compare, for example, a specific therapy to a placebo treatment as the interventions, "Crohn's disease" as the disease, and "remission" as the outcome. A user inputs the disease, interventions and outcomes (as text) and the system locates evidence that matches the disease, interventions and outcomes exactly or to similar diseases, interventions, and outcomes. "Similar" may refer to either word similarity or conceptual similarity. For example, "Crohn disease" and "Crohn's disease" demonstrate word similarity, while "Crohn's Disease" and "Inflammatory Bowel Disease" demonstrate conceptual similarity, since Crohn's disease is a specific case of the more general concept of inflammatory bowel disease.

In step 620, all of the matching, extracted evidence is analyzed to determine if there is an overall benefit in applying the interventions for the diseases to produce the outcomes. The analysis is done using statistical meta-analysis. Statistical meta-analysis may be the application of Random Effects Models, Fixed Effects Models, and Q-Score analysis.

In step 630, the system presents the user with the result of the statistical meta-analysis, along with details about each individual piece of evidence that constitute the meta-analysis. The results are presented as a combination of text descriptions, images, tabular information, and interactive components (such as excluding a paper and re-calculating the meta-analysis results on-the-fly).

Figure 7:
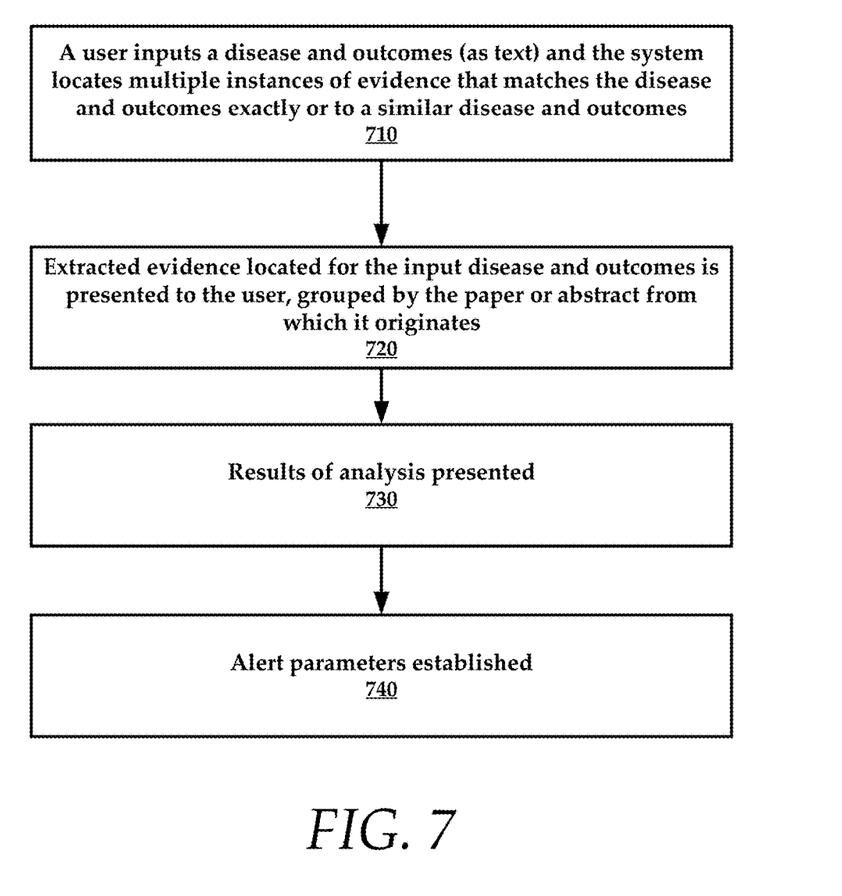
FIG. 7 is a flowchart of an additional example method of the present disclosure.

FIG. 7 illustrates an exemplary method to find the extracted evidence for a given disease and outcome.

In step 710, a user inputs a disease and outcomes (as text) and the system locates multiple instances of evidence that matches the disease and outcomes exactly or to similar diseases and outcomes. "Similar" in this context refers to either word similarity or conceptual similarity. For example, "Crohn disease" and "Crohn's disease" demonstrate word similarity, while "Crohn's Disease" and "Inflammatory Bowel Disease" demonstrate conceptual similarity, since Crohn's disease is a specific case of the more general concept of inflammatory bowel disease.

In step 720, all of the extracted evidence located for the input disease and outcomes is presented to the user, grouped by the paper or abstract from which it originates. This evidence may include the results, the interventions, details about the population, the original sentences from where the data is extracted, and information about the source paper or abstract (such as the paper title, journal name, and date). The results may be presented in a tabular format.

In step 730, if the system has sufficient data to perform a statistical meta-analysis, then those results are presented as well. A statistical meta-analysis computes an overall benefit by combining evidence using analysis methods that may be Random Effects Models, Fixed Effects Models or Q-Scores. The results are presented as a combination of text descriptions, images, tabular information and interactive components (such as excluding a paper and re-calculating the meta-analysis results on-the-fly).

In step 740, a user may set up alerts for their search criteria. These alerts will notify the user if there is new evidence related to their search, and if this new evidence results in changes to the statistical meta-analysis results from step 730. An alert may be an email notification or a mobile message notification.

Figure 8:
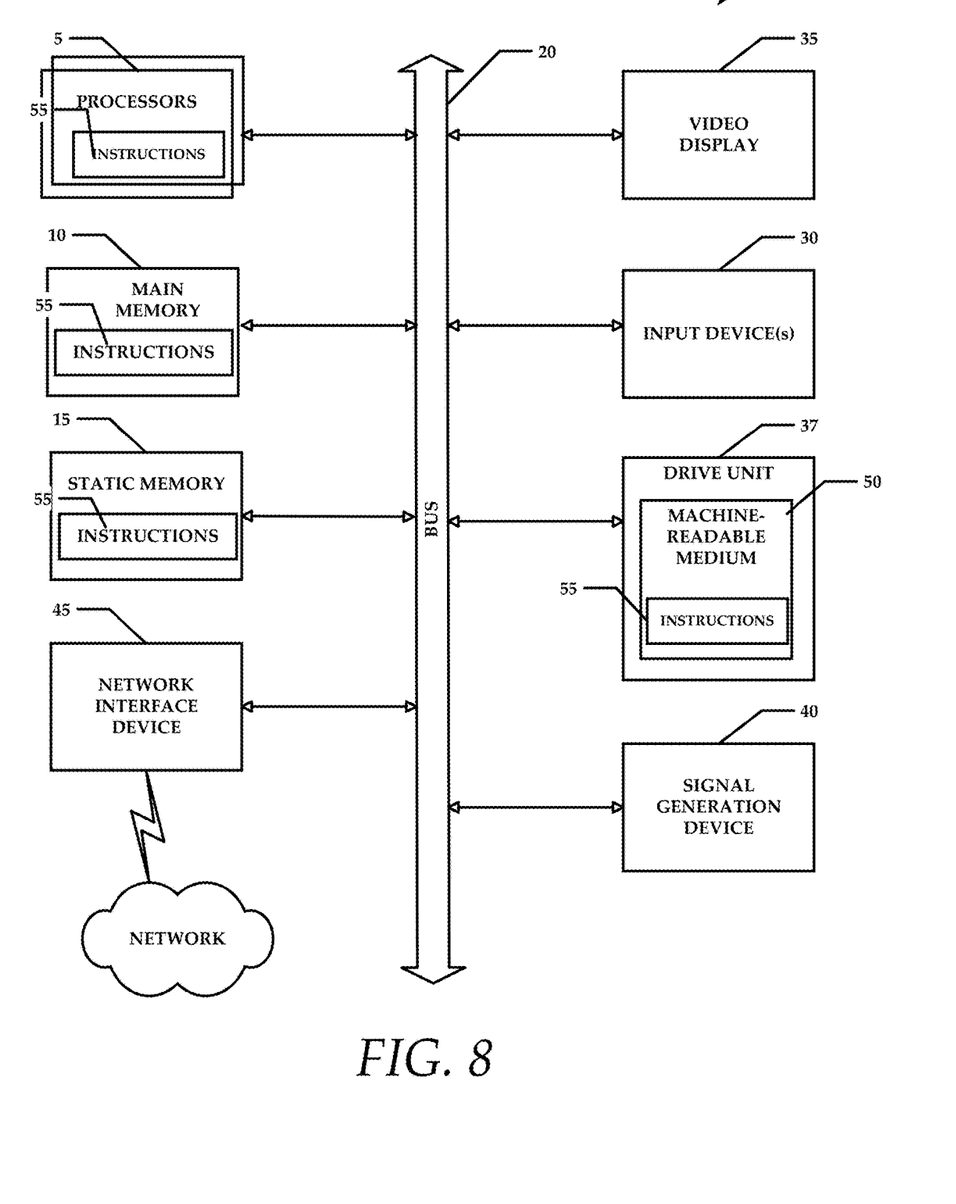
FIG. 8 is a diagrammatic representation of a computer system or a machine, within which a set of instructions for causing the machine to perform any one or more of the methodologies discussed herein, can be executed.

FIG. 8 is a diagrammatic representation of an example machine in the form of a computer system 1, within which a set of instructions for causing the machine to perform any one or more of the methodologies discussed herein may be executed. In various example embodiments, the machine operates as a standalone device or may be connected (e.g., networked) to other machines. In a networked deployment, the machine may operate in the capacity of a server or a client machine in a server-client network environment, or as a peer machine in a peer-to-peer (or distributed) network environment. The machine may be a robotic construction marking device, a base station, a personal computer (PC), a tablet PC, a set-top box (STB), a personal digital assistant (PDA), a cellular telephone, a portable music player (e.g., a portable hard drive audio device such as an Moving Picture Experts Group Audio Layer 3 (MP3) player), a web appliance, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 1 includes a processor or multiple processors 5 (e.g., a central processing unit (CPU), a graphics processing unit (GPU), or both), and a main memory 10 and static memory 15, which communicate with each other via a bus 20. The computer system 1 may further include a video display 35 (e.g., a liquid crystal display (LCD)). The computer system 1 may also include an alphanumeric input device(s) 30 (e.g., a keyboard), a cursor control device (e.g., a mouse), a voice recognition or biometric verification unit (not shown), a drive unit 37 (also referred to as disk drive unit), a signal generation device 40 (e.g., a speaker), and a network interface device 45. The computer system 1 may further include a data encryption module (not shown) to encrypt data.

The drive unit 37 includes a computer or machine-readable medium 50 on which is stored one or more sets of instructions and data structures (e.g., instructions 55) embodying or utilizing any one or more of the methodologies or functions described herein. The instructions 55 may also reside, completely or at least partially, within the main memory 10 and/or within the processors 5 during execution thereof by the computer system 1. The main memory 10 and the processors 5 may also constitute machine-readable media.

The instructions 55 may further be transmitted or received over a network via the network interface device 45 utilizing any one of a number of well-known transfer protocols (e.g., Hyper Text Transfer Protocol (HTTP)). While the machine-readable medium 50 is shown in an example embodiment to be a single medium, the term "computer-readable medium" should be taken to include a single medium or multiple media (e.g., a centralized or distributed database and/or associated caches and servers) that store the one or more sets of instructions. The term "computer-readable medium" shall also be taken to include any medium that is capable of storing, encoding, or carrying a set of instructions for execution by the machine and that causes the machine to perform any one or more of the methodologies of the present application, or that is capable of storing, encoding, or carrying data structures utilized by or associated with such a set of instructions. The term "computer-readable medium" shall accordingly be taken to include, but not be limited to, solid-state memories, optical and magnetic media, and carrier wave signals. Such media may also include, without limitation, hard disks, floppy disks, flash memory cards, digital video disks, random access memory (RAM), read only memory (ROM), and the like. The example embodiments described herein may be implemented in an operating environment comprising software installed on a computer, in hardware, or in a combination of software and hardware.

Not all components of the computer system 1 are required and thus portions of the computer system 1 can be removed if not needed, such as Input/Output (I/O) devices (e.g., input device(s) 30). One skilled in the art will recognize that the Internet service may be configured to provide Internet access to one or more computing devices that are coupled to the Internet service, and that the computing devices may include one or more processors, buses, memory devices, display devices, input/output devices, and the like. Furthermore, those skilled in the art may appreciate that the Internet service may be coupled to one or more databases, repositories, servers, and the like, which may be utilized in order to implement any of the embodiments of the disclosure as described herein.

As used herein, the term "module" may also refer to any of an application-specific integrated circuit ("ASIC"), an electronic circuit, a processor (shared, dedicated, or group) that executes one or more software or firmware programs, a combinational logic circuit, and/or other suitable components that provide the described functionality.

The corresponding structures, materials, acts, and equivalents of all means or step plus function elements in the claims below are intended to include any structure, material, or act for performing the function in combination with other claimed elements as specifically claimed. The description of the present technology has been presented for purposes of illustration and description, but is not intended to be exhaustive or limited to the present technology in the form disclosed. Many modifications and variations will be apparent to those of ordinary skill in the art without departing from the scope and spirit of the present technology. Exemplary embodiments were chosen and described in order to best explain the principles of the present technology and its practical application, and to enable others of ordinary skill in the art to understand the present technology for various embodiments with various modifications as are suited to the particular use contemplated.

Aspects of the present technology are described above with reference to flowchart illustrations and/or block diagrams of methods, apparatus (systems) and computer program products according to embodiments of the present technology. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present technology. In this regard, each block in the flowchart or block diagrams may represent a module, segment, or portion of code, which comprises one or more executable instructions for implementing the specified logical function (s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

In the following description, for purposes of explanation and not limitation, specific details are set forth, such as particular embodiments, procedures, techniques, etc. in order to provide a thorough understanding of the present invention. However, it will be apparent to one skilled in the art that the present invention may be practiced in other embodiments that depart from these specific details.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" or "according to one embodiment" (or other phrases having similar import) at various places throughout this specification are not necessarily all referring to the same embodiment. Furthermore, the particular features, structures, or characteristics may be combined in any suitable manner in one or more embodiments. Furthermore, depending on the context of discussion herein, a singular term may include its plural forms and a plural term may include its singular form. Similarly, a hyphenated term (e.g., "on-demand") may be occasionally interchangeably used with its non-hyphenated version (e.g., "on demand"), a capitalized entry (e.g., "Software") may be interchangeably used with its non-capitalized version (e.g., "software"), a plural term may be indicated with or without an apostrophe (e.g., PE's or PEs), and an italicized term (e.g., "N+1") may be interchangeably used with its non-italicized version (e.g., "N+1"). Such occasional interchangeable uses shall not be considered inconsistent with each other.

Also, some embodiments may be described in terms of "means for" performing a task or set of tasks. It will be understood that a "means for" may be expressed herein in terms of a structure, such as a processor, a memory, an I/O device such as a camera, or combinations thereof. Alternatively, the "means for" may include an algorithm that is descriptive of a function or method step, while in yet other embodiments the "means for" is expressed in terms of a mathematical formula, prose, or as a flow chart or signal diagram.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

If any disclosures are incorporated herein by reference and such incorporated disclosures conflict in part and/or in whole with the present disclosure, then to the extent of conflict, and/or broader disclosure, and/or broader definition of terms, the present disclosure controls. If such incorporated disclosures conflict in part and/or in whole with one another, then to the extent of conflict, the later-dated disclosure controls.

The terminology used herein can imply direct or indirect, full or partial, temporary or permanent, immediate or delayed, synchronous or asynchronous, action or inaction. For example, when an element is referred to as being "on," "connected" or "coupled" to another element, then the element can be directly on, connected or coupled to the other element and/or intervening elements may be present, including indirect and/or direct variants. In contrast, when an element is referred to as being "directly connected" or "directly coupled" to another element, there are no intervening elements present. The description herein is illustrative and not restrictive. Many variations of the technology will become apparent to those of skill in the art upon review of this disclosure.

While various embodiments have been described above, it should be understood that they have been presented by way of example only, and not limitation. The descriptions are not intended to limit the scope of the invention to the particular forms set forth herein. To the contrary, the present descriptions are intended to cover such alternatives, modifications, and equivalents as may be included within the spirit and scope of the invention as defined by the appended claims and otherwise appreciated by one of ordinary skill in the art. Thus, the breadth and scope of a preferred embodiment should not be limited by any of the above-described exemplary embodiments.

What is claimed is:

1. A method, comprising:
   extracting content for each of a plurality of types from a corpus of textual information, the plurality of types corresponding to segments of an inference scheme, the inference scheme comprising a dependency that orders the segments together so as to create a summation of the corpus of textual information when the extracted content is assembled;
   assembling one or more inferred statements using the inference scheme and the extracted content; and receiving user feedback that comprises a correction to the one or more inferred statements.

2. The method according to claim 1, wherein extracting content further comprises tagging parts of speech for words within the corpus of textual information that correspond to one or more of the plurality of types.

3. The method according to claim 2, wherein extracting content further comprises locating phrase chunks within the corpus of textual information that correspond to one or more of the plurality of types.

4. The method according to claim 3, wherein extracting content further comprises determining synonyms for at least a portion of the words.

5. The method according to claim 4, wherein the plurality of types comprises any of a condition, an inclusion criterion, an intervention, a population size, and an outcome.

6. The method according to claim 5, further comprising executing an extractor for each of the plurality of types.

7. The method according to claim 1, wherein the corpus of textual information comprises sentences and the extraction of content occurs across a plurality of sentences in the corpus of textual information.

8. The method according to claim 1, further comprising updating an extraction algorithm used to extract the content based on the user feedback.

9. The method according to claim 1, further comprising receiving user feedback when no content is found within the corpus of textual information for at least one of the plurality of types, the user feedback comprising an identification of a keyword within the corpus of textual information that is identified as being a word that belongs to the at least one of the plurality of types.

10. A system comprising:
a processor; and
a memory for storing executable instructions, the processor executing the instructions to:
execute a plurality of extractor modules to extract evidence from each of a plurality of types from a medical study, the plurality of types corresponding to segments of an inference scheme, the inference scheme comprising a dependency that orders the segments together so as to create a summation of the medical study when the extracted evidence is assembled;
execute an assembly module that assembles one or more inferred statements about the medical study using the inference scheme and the extracted evidence; and
a user interface for interacting with results extracted from one or more studies that enables users to correct results, augment the results, and assess overall treatment effectiveness.

11. The system according to claim 10, wherein each of the plurality of extractor modules is further configured to tag parts of speech for words within the medical study that correspond to one or more of the plurality of types.

12. The system according to claim 11, wherein each of the plurality of extractor modules is further configured to locate phrase chunks within the medical study that correspond to one or more of the plurality of types.

13. The system according to claim 10, wherein each of the plurality of extractor modules is further configured to determine synonyms for at least a portion of words.

14. The system according to claim 10, wherein each of the plurality of extractor modules implements an extraction algorithm for extracting any of the plurality of types comprising interventions used, treatment results, treatment effectiveness, outcomes targeted, and diseases targeted, and any combinations thereof.

15. The system according to claim 14, wherein each of the plurality of extractor modules utilizes a combination of pattern matching and statistical inference for extracting and machine learning.

16. The system according to claim 15, further comprising a statistical meta-analysis module capable of combining the evidence extracted from more than one medical study and computing a statistical score that represents an overall effectiveness of treatment based on the combined evidence.

17. The system according to claim 10, further comprising a dependency parser executed to select and apply the inference scheme in combination with the plurality of extractor modules.

* * * * *